(12) United States Patent
Nakazawa

(10) Patent No.: US 6,611,331 B2
(45) Date of Patent: Aug. 26, 2003

(54) METHOD OF MEASURING SURFACE FORM OF SEMICONDUCTOR THIN FILM

(75) Inventor: Makoto Nakazawa, Miyagi (JP)

(73) Assignee: Oki Electric Industry Co., Ltd., Tokyo (JP)

(*) Notice: Subject to any disclaimer, the term of this patent is extended or adjusted under 35 U.S.C. 154(b) by 0 days.

(21) Appl. No.: 10/218,242

(22) Filed: Aug. 15, 2002

(65) Prior Publication Data

US 2002/0191187 A1 Dec. 19, 2002

Related U.S. Application Data

(62) Division of application No. 09/652,264, filed on Aug. 30, 2000, now Pat. No. 6,476,912.

(30) Foreign Application Priority Data

Mar. 1, 2000 (JP) ........................................ 2000-055603

(51) Int. Cl.⁷ .............................. G01J 4/00; G01B 11/24
(52) U.S. Cl. ..................... 356/369; 356/601; 356/600
(58) Field of Search ................................ 356/369, 601, 356/600, 437

(56) References Cited

U.S. PATENT DOCUMENTS

| | | | |
|---|---|---|---|
| 5,399,229 A | | 3/1995 | Stefani et al. |
| 5,526,117 A | | 6/1996 | Wielsch et al. |
| 5,624,190 A | | 4/1997 | Joseph et al. |
| 5,753,530 A | * | 5/1998 | Akamine et al. ........... 438/560 |
| 5,929,994 A | | 7/1999 | Lee et al. |
| 6,031,614 A | * | 2/2000 | Michaelis et al. .......... 356/369 |
| 6,060,400 A | * | 5/2000 | Oehrlein et al. ............ 438/706 |
| 6,128,084 A | * | 10/2000 | Nanbu et al. ............... 356/369 |

\* cited by examiner

Primary Examiner—Frank G. Font
Assistant Examiner—Roy M. Punnoose
(74) Attorney, Agent, or Firm—Volentine Francos, PLLC

(57) ABSTRACT

The surface form of a semiconductor thin film such as a polysilicon film formed on a semiconductor substrate is measured through spectro-ellipsometry or measured by performing an IPA quantitative analysis through GC. Mass (gas chromatography) after exposing the semiconductor thin film to IPA (isopropyl alcohol) vapor and drying the semiconductor thin film. Through either of these methods, the surface form of the polysilicon film can be easily and quickly measured.

11 Claims, 16 Drawing Sheets

FIG.5

| Layer | Comp.1 | Comp.2 | Concentration | Thickness |
|---|---|---|---|---|
| first layer | r-poly | void | 0.562823 | 0.010226 |
| second layer | r-poly | void | 0.311958 | 0.055009 |
| third layer | r-poly | void | 0.766849 | 0.020310 |
| fourth layer | r-poly | siam2 | 0.341908 | 0.007380 |
| fifth layer | sio2 | — | — | 0.050000 |
| Substrate | sicr | — | — | ∞ |

FIG.6

| | Comp.1 | Comp.2 | Void Rate | Film Thickness |
|---|---|---|---|---|
| first layer | r-poly | void | 0.552727(V1) | 0.008488(T1) |
| second layer | r-poly | void | 0.286094(V2) | 0.0507784(T2) |
| third layer | r-poly | void | 0.798009(V3) | 0.021734(T3) |
| fourth layer | r-poly | siam2 | 0.305800(V4) | 0.006905(T4) |
| fifth layer | sio2 | — | — | 0.050000 |
| Semiconductor Substrate | sicr | — | — | ∞ |

FIG.9
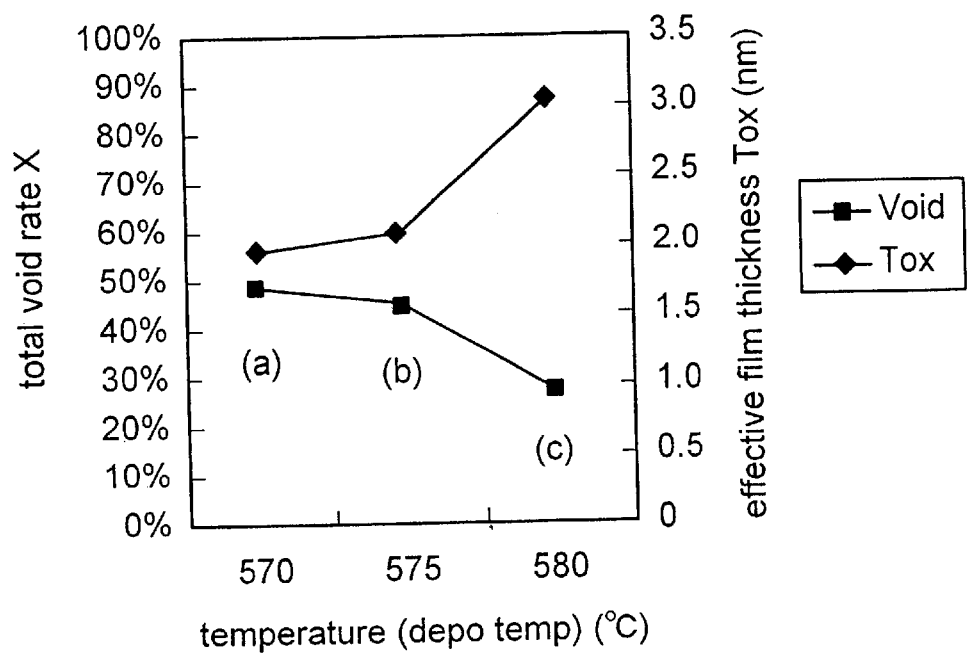
FIG.10(a)  FIG.10(b)  FIG.10(c)
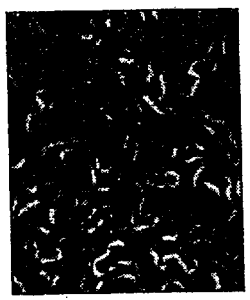
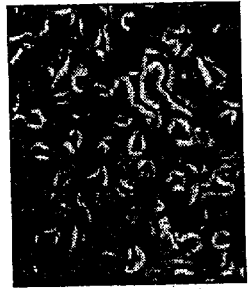
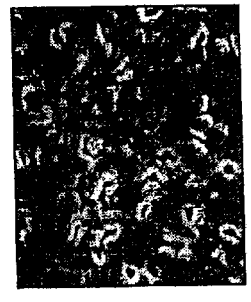
Depo Temp 570 °C | Depo Temp 575 °C | Depo Temp 580 °C FIG.11
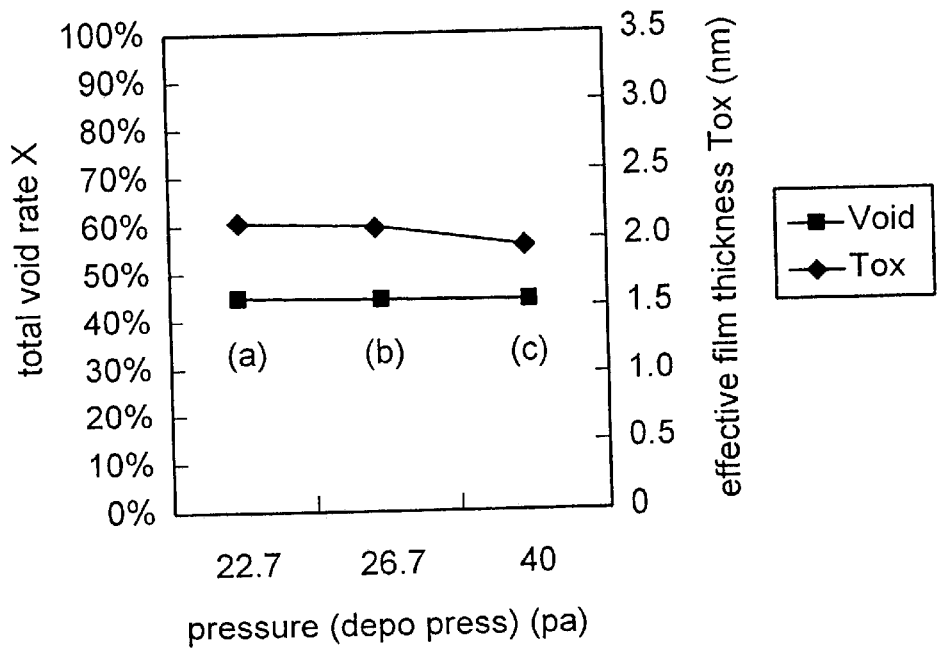
FIG.12(a)        FIG.12(b)        FIG.12(c)
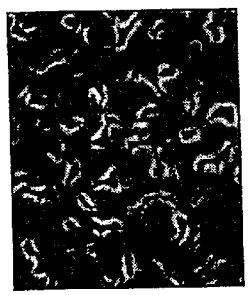    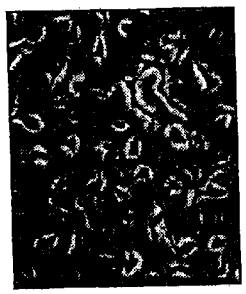    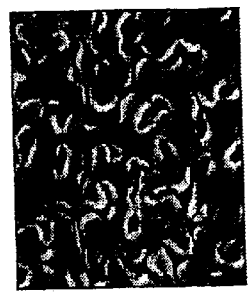
Depo Press 22.7Pa    Depo Preaa 26.7Pa    Depo Press 40Pa Depo Time 7min Depo Time 11min Depo Time 15min Depo Time 19min 575°C, 40Pa, 19min 570°C, 26.7Pa, 19min 575°C, 22.7Pa, 11min 580°C, 22.7Pa, 15min FIG.18
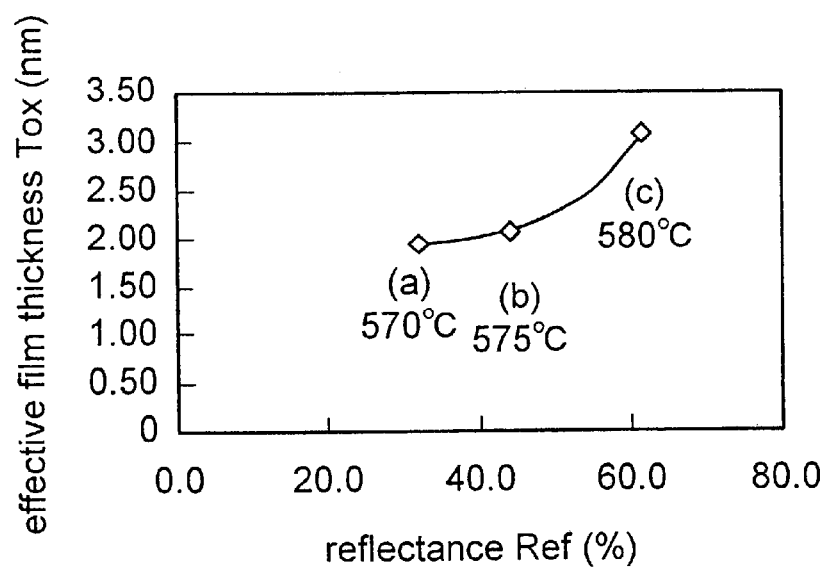
FIG.19(a)  FIG.19(b)  FIG.19(c)
  
570°C  575°C  580°C 40Pa 26.7Pa 22.7Pa FIG.22
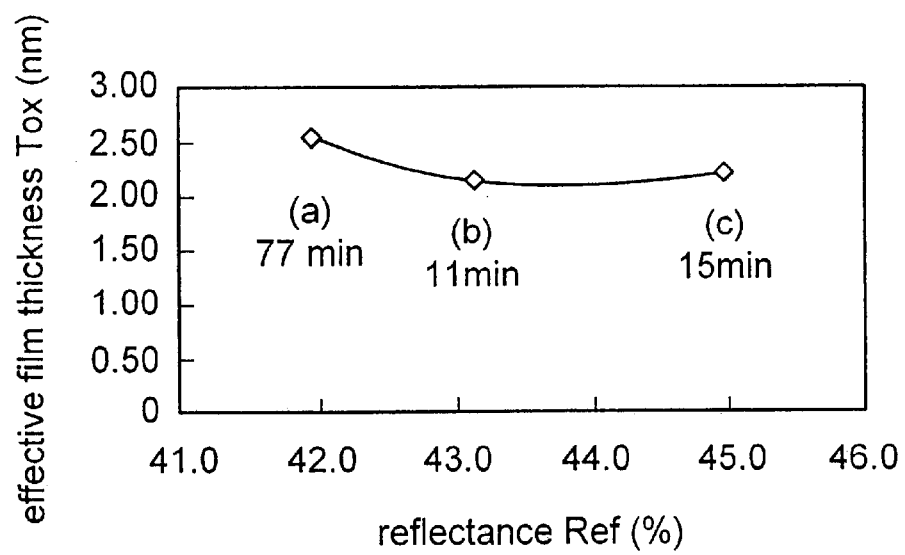
FIG.23(a)     FIG.23(b)     FIG.23(c)
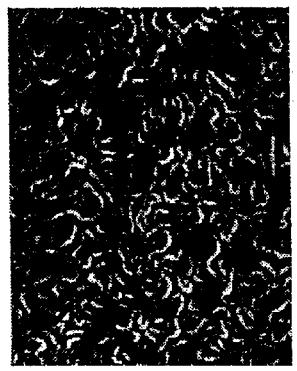    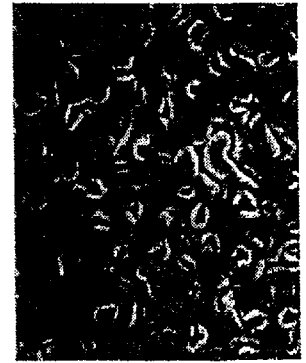
7min          11min         15min

METHOD OF MEASURING SURFACE FORM OF SEMICONDUCTOR THIN FILM

This is a divisional application of application Ser. No. 09/652,264, filed Aug. 30, 2000, U.S. Pat. No. 6,476,912 B1 which is hereby incorporated by reference in its entirety for all purposes.

BACKGROUND OF THE INVENTION

1. Field of the Invention

The present invention relates to a method of measuring the surface form of a semiconductor thin film and, more specifically, it relates to a method of measuring the surface form of a polysilicon film formed on a semiconductor substrate to constitute a capacitor electrode.

2. Description of the Related Art

A semiconductor memory element such as a DRAM (dynamic random access memory) is provided with numerous capacitors. Capacitors formed at such a memory element are formed by laminating a lower electrode, a dielectric film and an upper electrode on a semiconductor substrate. In recent years, the application of the technology whereby the capacities of the capacitors formed at memory elements are increased by forming indentations and projections at the surface of the capacitor electrode constituted of a polysilicon film facing opposite the dielectric film and, therefore, increasing the surface area of the dielectric film has become common.

Since the charge storage capacity of a capacitor is affected by the degree/height of the indentations and projections formed at the surface of the capacitor electrode, consistency must be achieved in the degree/height of the indentations and projections formed at the surface of the capacitor electrode in order to achieve consistency in the charge storage capacity of the capacitor. For this reason, the surface form of the capacitor electrode must be measured.

Instead of directly measuring the surface form of the capacitor electrode, a method in which the thickness of the capacitor electrode, i.e., the film thickness of the polysilicon film, is measured is adopted in the prior art. Since the surface form of the capacitor electrode cannot be directly observed on an AFM (atomic force microscope), a direct examination is always implemented by utilizing an SEM (scanning electron microscope).

The surface form of the capacitor electrode, which has a close correlation to the capacitor capacity is one of the most crucial production management items and must be closely controlled in order to provide high-quality memory elements. If an abnormality is found in polysilicon film thickness measurement during a memory element manufacturing stage, it should be assumed that the surface form of the capacitor electrode does not meet the specifications. Accordingly, the conditions under which the polysilicon film is formed must be reassessed. However, it is not possible to accurately ascertain the surface form of the capacitor electrode in correspondence to the film thickness of the polysilicon film. Thus, it is difficult to promptly determine the optimal film forming conditions under which the polysilicon film should be formed in order to achieve the desired surface form for the capacitor electrode.

Observing the surface form of the capacitor electrode with an SEM, on the other hand, is a laborious process, requiring a great deal of time. As a result, it reduces the productivity in semiconductor element production.

SUMMARY OF THE INVENTION

An object of the present invention is to provide a method of measuring the surface form of a semiconductor thin film such as a polysilicon film quickly and easily.

Accordingly, the present invention provides a method of measuring the surface form of a semiconductor thin film formed at a surface of a semiconductor substrate. The method, which comprises a step in which a graph representing the relationship between tan $\phi$ and the measurement wavelength and a graph representing the relationship between cos $\Delta$ and the measurement wavelength with regard to the semiconductor thin film are prepared through spectro-ellipsometry, a step in which the film thickness of the semiconductor thin film is optimized by optimizing a coefficient in a Cauchy model function on the premise that five layers of film are laminated on the surface of the semiconductor substrate with film thicknesses T1, T2, T3 and T4 and void rates V1, V2, V3 and V4 respectively corresponding to a first layer, a second layer, a third layer and a fourth layer of the semiconductor thin film starting from the side toward the semiconductor thin film surface among the five layers are ascertained by fitting the optimized film thickness in the graph representing the relationship between tan $\phi$ and the measurement wavelength and the graph representing the relationship between cos $\Delta$ and the measurement wavelength and a step in which the values thus ascertained are used for substitution in the following expression (1) to calculate a total void rate X:

$$X = (T1 \times V1 + T2 \times V2 + T3 \times V3)/(T1 + T2 + T3) \qquad (1)$$

is characterized in that the surface form of the semiconductor thin film is measured based upon a correlation between the total void rate X and the surface form of the semiconductor thin film.

According to the present invention, the surface form of the semiconductor thin film may refer to, for instance, the surface area of the semiconductor thin film, and in the case of a memory element having numerous capacitors such as a DRAM (dynamic random access memory), it represents an index of the capacitor capacity, i.e., an index of the effective film thickness.

In addition, the present invention provides a method of measuring the surface form of a semiconductor thin film, which is achieved by uniformly depositing IPA on the surface of the semiconductor thin film formed at a surface of a semiconductor substrate, performing a quantitative analysis of IPA released from the surface of the semiconductor thin film and measuring the surface form of the semiconductor thin film based upon a correlation between the quantity of IPA thus detected and the surface form of the semiconductor thin film.

BRIEF DESCRIPTION OF THE DRAWINGS

The above and other features of the invention and the concomitant advantages will be better understood and appreciated by persons skilled in the field to which the invention pertains in view of the following description given in conjunction with the accompanying drawings which illustrate preferred embodiments. In the drawings:

FIG. 5 presents a table of the value settings in the spectro-ellipsometry used for reference in graph fitting in implementation 1;

FIG. 6 presents a table of film thicknesses and void rates corresponding to the first layer, the second layer, the third layer and the fourth layer ascertained in implementation 1;

FIG. 9 presents a graph of the relationship between the total void rate X and the effective film thickness Tox achieved by varying the temperature during the polysilicon film formation in implementation 1;

FIG. 10 presents photographs of the polysilicon films (a), (b) and (c) in FIG. 9 observed through an SEM;

FIG. 11 presents a graph of the relationship between the total void rate X and the effective film thickness Tox achieved by varying the pressure during the polysilicon film formation in implementation 1;

FIG. 12 presents photographs of the polysilicon films (a), (b) and (c) in FIG. 11 observed through an SEM;

FIG. 18 presents a graph of the relationship between the reflectance Ref and the effective film thickness Tox achieved by varying the film formation temperature during the polysilicon film formation in implementation 3;

FIG. 19 presents photographs of the polysilicon films (a), (b) and (c) in FIG. 18 observed through an SEM;

FIG. 22 presents a graph of the relationship between the reflectance Ref and the effective film thickness Tox achieved by varying the film formation duration during the polysilicon film formation in implementation 3; and FIG. 23 presents photographs of the polysilicon films (a), (b) and (c) in FIG. 22 observed through an SEM.

DETAILED DESCRIPTION OF THE PREFERRED EMBODIMENTS

Figure 1:
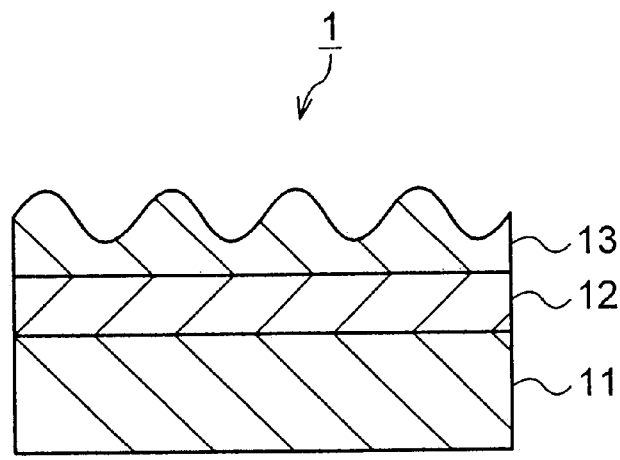
FIG. 1 is a sectional view of a semiconductor element.

The following is an explanation of preferred embodiments of the present invention, given in reference to the drawings. FIG. 1 is a sectional view of a semiconductor element 1 used in the embodiments of the invention. At a surface (the upper surface in FIG. 1) of a semiconductor substrate 11, a thermal oxide film 12 is developed over a thickness of, for instance, approximately 50 nm, and a polysilicon film 13 constituting a semiconductor thin film is formed over the thermal oxide film 12.

In a first embodiment of the present invention, by measuring the semiconductor element 1 by varying the measurement wavelength within the range of 0.25~0.85 μm through spectro-ellipsometry to obtain a graph of the relationship between tan φ and the measurement wavelength and a graph of the relationship between cos Δ and the measurement wavelength.

Ellipsometry refers to a method of analysis whereby elliptically polarized laser light is irradiated onto the surface of an object and changes (tan φ and cos Δ) in the state of the elliptically polarized light reflected by the object are ascertained to determine the characteristics of the object surface (film thickness, refractive index) in correspondence to tan φ and cos Δ. Ellipsometry includes single wavelength ellipsometry through which measurement is performed using laser light with a constant wavelength (e.g., 0.633 μm) and spectro-ellipsometry through which tan φ and cos Δ are ascertained by varying the wavelength of the laser light (e.g., 0.25~0.85 μm). In spectro-ellipsometry, the semiconductor element 1 to be examined is placed on a test piece stage and a light that has passed through, for instance, a polarizer and a quarter wave plate is made to enter the semiconductor element 1. Reflected light from the semiconductor element 1 is made to enter a detector after passing through, for instance, an analyzer.

Light that enters the surface of the semiconductor element 1 in spectro-ellipsometry (performed on an ellipsometric film thickness measurement device) contains a coefficient of reflection parallel to the plane of incidence and a coefficient of reflection perpendicular to the plane of incidence. A measurement value is expressed as the ratio of these coefficients. Tan φ and cos Δ indicate a coefficient ratio, and since coefficient ratios are obtained over the full wavelength range in spectro-ellipsometry, tan φ and cos Δ are represented as curves shown in FIGS. 3 and 4 which are to be explained later.

In more specific terms, light having an equal amplitude ratios with respect to the S polarized light component constituting an oscillation component parallel to the surface of the object (test piece surface) and the P polarized light component constituting an oscillation component perpendicular to the direction in which the light advances and also perpendicular to the S polarized light component is irradiated and the polarization state of the reflected light is detected. In the measurement results, the ratio ρ of the amplitude reflection coefficient of the S polarized light component to the amplitude reflection coefficient of the P polarized light component is obtained as tan φ and the phase difference between the P polarized light component and the S polarized light component is obtained as cos Δ.

In addition, the thickness of the polysilicon film 13 in the semiconductor element 1 is optimized by optimizing a coefficient in a Cauchy model function on a premise that five layers of the film are laminated at the surface of the semiconductor substrate 11 and film thicknesses T1, T2, T3 and T4 and void rates V1, V2, V3 and V4 respectively corresponding to a first layer, a second layer, a third layer and a fourth layer in the semiconductor thin film starting from the side toward the semiconductor thin film surface among the five layers are ascertained by fitting the optimized thickness of the polysilicon film 13 into the graph of the relationship between tan φ and the measurement wavelength and the graph of the relationship between cos Δ and the measurement wavelength.

The Cauchy model function is expressed as;

$$\Delta n(\lambda)=A+B/\lambda^2$$

(Δn: birefringent anisotropy, A, B: constant, λ: wavelength of measuring light).

Figure 2:
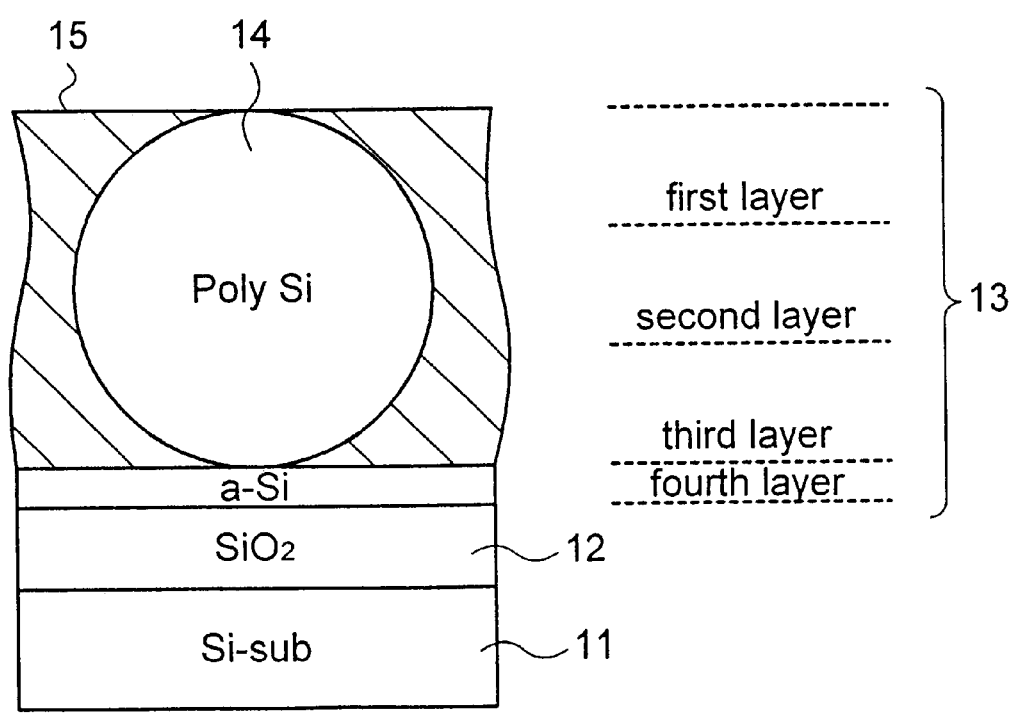
FIG. 2 illustrates the definition of the 5-layer film in spectro-ellipsometry.

FIG. 2 illustrates the definition of the five layer film structure with five layers of film laminated over the surface of the semiconductor substrate 11. As shown in FIG. 2, the polysilicon film 13 formed on the thermal oxide film 12 at the surface of the semiconductor substrate 11 is divided into four layers, with the thermal oxide film 12 constituting the fifth layer. Starting on the side toward the surface of the polysilicon film 13, the first, second layer and third layers constituted of polysilicon particles (rough surface particles) 14 and the fourth layer constitutes a transition region (a-Si) between the thermal oxide film 12 and the polysilicon film 13. In the polysilicon film 13, the first through third layers have indentations and projections, with air present in the shaded area 15 around the polysilicon particles 14 creating voids.

While the Sellmeier model, the Lorentz model, the Drude model or the like may be used for polynomial approximation instead of the Cauchy model, it is desirable to use the Cauchy model if the optical constant of the film laminated on the surface of the semiconductor substrate 11 is known in advance as in the present invention.

The coefficient optimization is synonymous with graph fitting. Graph fitting refers to a comparison of a known optical constant of film which may be theoretically ascertained or set in advance with the results of actual measurement. Through graph fitting, the optical constants over the full wavelength range are incorporated in the measured values and, as a result, the film thickness of the film undergoing measurement is ascertained.

In the graph fitting in the embodiment, the individual curves corresponding to tan φ and cos Δ in a standard model are assimilated (exactly matched, preferably) to the curves obtained through the measurement by varying the film thicknesses and the concentrations of the individual layers in a standard model of the polysilicon film 13.

In order to implement such graph fitting, it is necessary to prepare a standard model for the polysilicon film 13. Accordingly, a polysilicon film 13 formed on the thermal oxide film 12 under standard conditions is used as the standard model. It is necessary to provide a standard model since the polysilicon film 13 is divided into four layers and if numerical values that are too far off are used for the film thicknesses and concentrations of the individual layers, the number of factors that must be changed during the graph fitting process increases to present a hindrance to achieving good graph fitting.

It is to be noted that a polysilicon film 13 achieving the largest surface area within a given plane is used as the standard model. A polysilicon film 13 achieving only a small surface area (achieving a small capacity as a capacitor) due to parameter fluctuations (fluctuations in the pressure, the gas flow rate and the temperature) occurring during the film formation is not suited for a standard model.

The polysilicon particles 14 span the first~third layers, as illustrated in FIG. 2 for the following reasons. Namely, the results of measurement of the surface form of the polysilicon film 13 performed by obtaining in advance standard models on the premise that the polysilicon particles 14 constitute two layers, three layers and four layers indicated that the value measured by assuming that the polysilicon particles 14 constitute three layers was the most reliable. The reliability was confirmed in the following manner. First, a film different from the optimal polysilicon film 13 was formed by intentionally changing the film formation conditions for forming the polysilicon film 13. Next, a monitor and a device were prepared by forming the polysilicon film 13 over the base film, i.e., the thermal oxide film 12 ($SiO_2$, 1000 Å). Then, void rates were measured for the monitor thus prepared by considering the polysilicon particles 14 to constitute two layers, three layers and four layers. In addition, the capacitor capacity was measured with regard to the device, and the regularity existing in the relationship between the void rates of the monitor and the capacitor capacity of the device was examined. The results of the examination indicated that the highest degree of regularity between the void rates and the capacitor capacity ascertained with regard to the device was achieved in the model obtained by considering that the polysilicon particles 14 constitute three layers.

Then, a standard value setting is input to a spectroellipsometer to perform graph fitting. Thus, the film thicknesses T1, T2, T3 and T4 corresponding to the first layer, the second layer, the third layer and the fourth layer and the void rates V1, V2, V3 and V4 corresponding to the first layer, the second layer, the third layer and the fourth layer are ascertained.

Next, these values are incorporated for substitution in the following expression (1) to determine the total void rate X.

$$X=(T1\times V1+T2\times V2+T3\times V3)/(T1+T2+T3) \quad (1)$$

Based upon the correlation between the total void rate X thus determined and the surface form of the polysilicon film 13, the surface form of the polysilicon film 13 can be measured.

In a second embodiment of the present invention, IPA is uniformly deposited on to a surface of the semiconductor element 1 illustrated in FIG. 1. Since the reproduceability of the IPA quantitative analysis to be performed later is compromised if IPA is not deposited uniformly, IPA must be deposited uniformly over the surface of the semiconductor element 1. In order to uniformly deposit IPA, the surface of the semiconductor element 1 may be exposed to IPA vapor and then dried, for instance.

Then, a quantitative analysis of IPA released from the surface of the polysilicon film 13 is performed through GC.Mass (gas chromatography). Thus, based upon the correlation between the IPA detection quantity and the surface form of the polysilicon film 13, the surface form of the polysilicon film 13 can be measured.

In the first and second embodiments of the present invention described above, the surface form of the semiconductor thin film such as the polysilicon film 13 formed over the surface of the semiconductor substrate 11 at the semiconductor element 1 shown in FIG. 1 can be measured quickly and easily. The surface form of the 13 determined in the first and second embodiments indicates the surface area of the polysilicon film 13, and in the case of a memory element having numerous capacitors such as a DRAM (dynamic random access memory), it represents an index of the capacitor capacity, i.e., an index of the effective film thickness. Thus, by adopting the first or the second embodiment, it becomes possible to accurately ascertain the degree and the height of indentations and projections formed at the surface of the capacitor electrodes in, for instance, a DRAM so that consistent charge storage capacity is achieved.

It is to be noted that while an explanation is given above in reference to the first and second embodiments of the invention on an example in which the surface form of a polysilicon film is measured, the present invention may be adopted in measurement of the surface form of a semiconductor thin film other than a polysilicon film such as in measurement of the surface form of a layer insulating film constituting part of a semiconductor element to detect an abnormal void and the like in the film. In particular, the measurement can be implemented to enable quantification of the shape of contact holes formed to connect two wiring layers provided with a layer insulating film present between them at a semiconductor element by adopting the second embodiment.

Next, the present invention was implemented in various modes using the semiconductor element 1 illustrated in FIG. 1 to examine its advantages.

Figure 3:
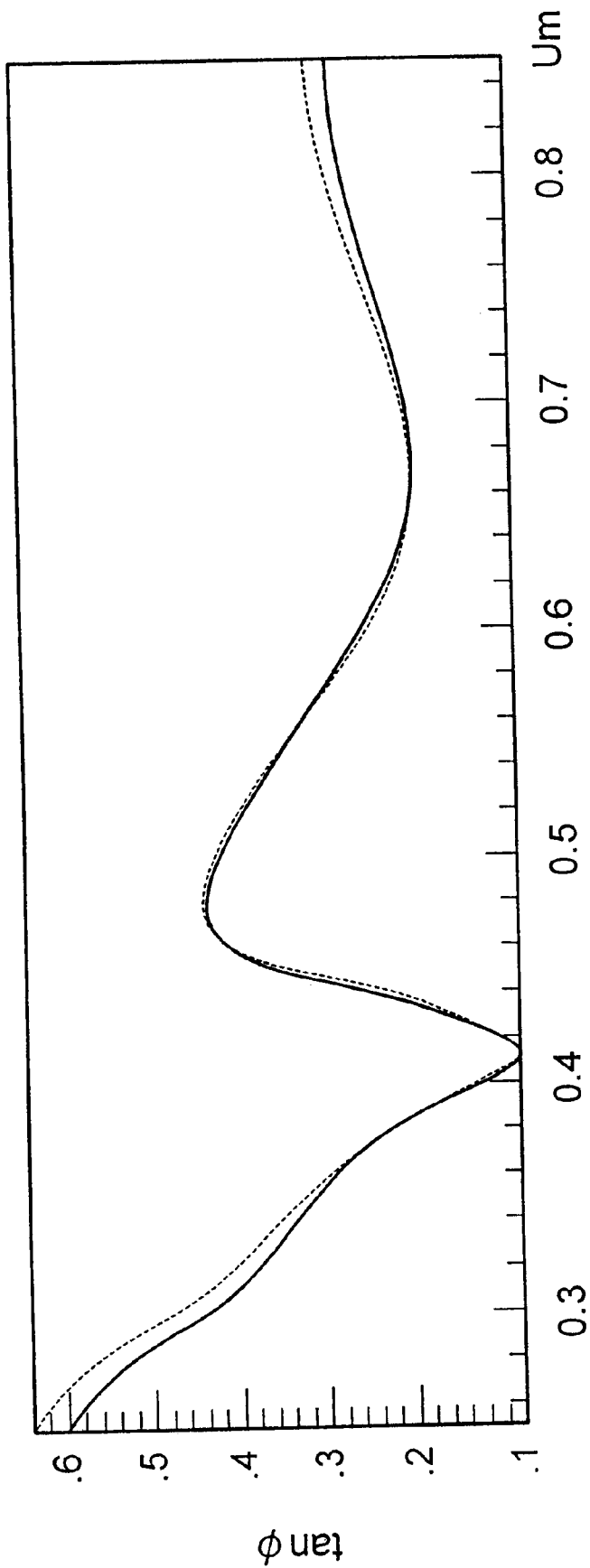
FIG. 3 presents a graph of tan $\phi$ obtained in implementation 1.
Figure 4:
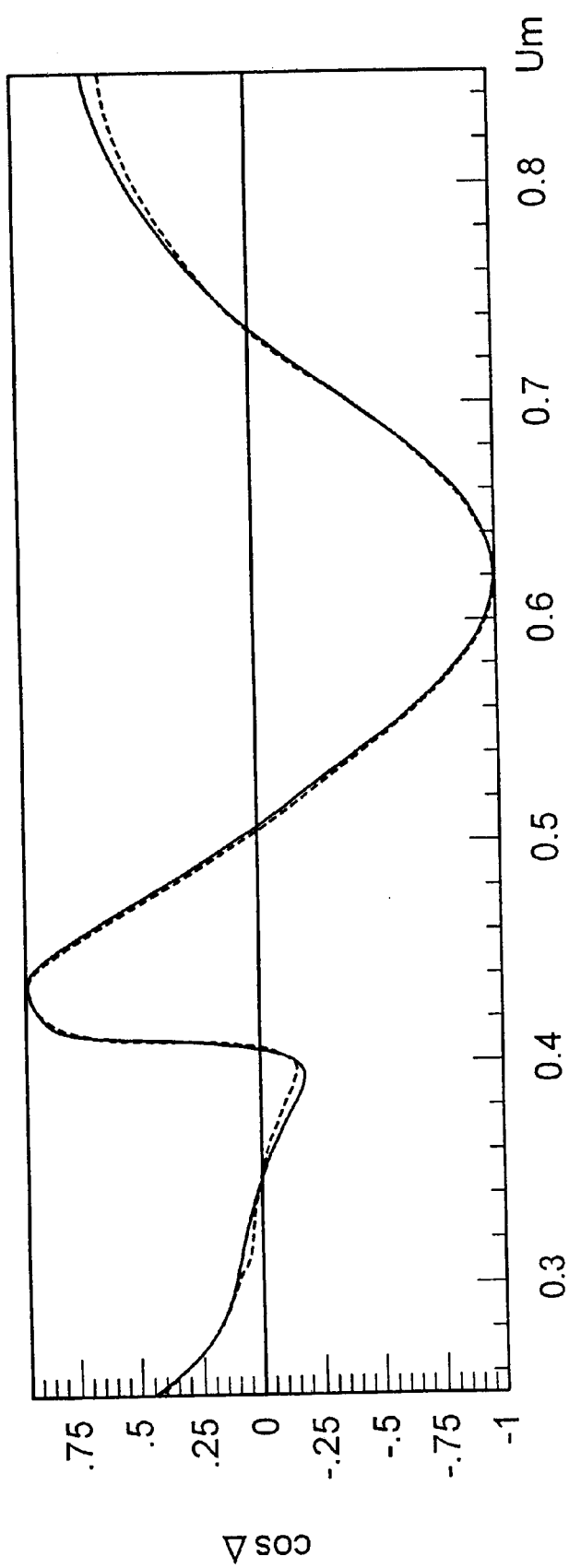
FIG. 4 presents a graph of cos $\Delta$ obtained in implementation 1.

First, the surface form of the polysilicon film constituting the semiconductor thin film was measured. As explained earlier in reference to FIG. 1, the thermal oxide film 12 was developed over a thickness of 50 nm at the surface of the semiconductor substrate 11, and the polysilicon film 13 was formed on the thermal oxide film 12 to constitute the semiconductor thin film. By measuring the polysilicon film 13 thus formed through spectro-ellipsometry over a wavelength range of 0.25~0.85 $\mu$m, tan $\phi$ was ascertained as illustrated in FIG. 3 and cos $\Delta$ was ascertained as illustrated in FIG. 4. In FIG. 3, the vertical axis represents tan $\phi$ and the horizontal axis represents the measurement wavelength in the spectro-ellipsometry, and in FIG. 4, the vertical axis represents cos $\Delta$ and the horizontal axis represents the measurement wavelength in spectro-ellipsometry. FIGS. 3 and 4 indicate the relationships between tan $\phi$ and the measurement wavelength and between cos $\Delta$ and the measurement wavelength achieved through the graph fitting process. FIGS. 3 and 4 each show two curves, one of which is the theoretical curve with the other being a curve graph fitted with the theoretical curve (however, in either FIG. 3 or 4, the theoretical curve and the graph fitted curve are almost completely aligned due to highly accurate graph fitting).

In addition, as explained earlier in reference to FIG. 2, it is assumed that a 5-layer film is formed at the surface of the semiconductor substrate 11. In the polysilicon film 13 formed over the thermal oxide film 12, the first layer, the second layer and the third layer are each constituted of the polysilicon particles, the fourth layer constitutes a transition region between the thermal oxide film 12 and the polysilicon film 13 and the fifth layer is constituted of the thermal oxide film 12. Then, the coefficient is optimized by using the Cauchy model function also the film thickness of the polysilicon film was optimized and graph fitting was implemented.

FIG. 5 presents value settings at the spectroellipsometer used as reference in the graph fitting process. In FIG. 5, "Comp.1" indicates the composition of each layer. "r-poly" indicates a rough surface polysilicon film, "sio2" indicates a silicon oxide film and sicr indicates an Si-sub (silicon substrate). "Comp.2" indicates the film quality of each layer with its composition defined in "Comp.1". "void" indicates that air pockets are present in the film and "siam 2" indicates that the film is in an amorphous state. Standard values that are determined to achieve the best graph fitting for tan $\phi$ and cos $\Delta$ obtained by measuring a standard rough surface polysilicon film are set for "concentration" and "film thickness" for each layer.

Through the graph fitting process, the individual film thicknesses T1, T2, T3 and T4 corresponding to the first layer, the second layer, the third layer and the fourth layer and the individual void rates V1, V2, V3 and V4 corresponding to the first layer, the second layer, the third layer and the fourth layer presented in FIG. 6 were determined. These values were then used for substitution in the following expression (1) to calculate the total void rate X.

$$X=(T1\times V1+T2\times V2+T3\times V3)/(T1+T2+T3) \quad (1)$$

The film thickness of a given layer affects the manner in which light is reflected. Since an air pocket in the layer may absorb light, the concentration in the layer affects the reflection of light. The amplitude reflection factor ratio $\rho$, which indicates of the polarization state of reflected light may be expressed as a function of the individual film thicknesses T1~T4 and the individual void rates V1, V2, V3 and V4.

$$\rho=f(T1,T2,T3,T4,V1,V2,V3,V4,) \quad (2)$$

In addition the amplitude reflection factor ratio $\rho$ may be ascertained in correspondence to tan $\phi_a$ and cos $\Delta_a$. The measurement values tan $\phi_a$ and cos $\Delta_a$ with regard to the polysilicon film 13 are detected through spectro-ellipsometry. By using appropriate values for the individual film thicknesses T1, T2, T3 and T4 and the individual void rates V1, V2, V3 and V4 for substitution in a specific model functional expression in which coefficients are optimized, values tan $\phi_b$ and cos $\Delta_b$ are calculated. If the measurement values tan $\phi_a$ and cos $\Delta_a$ and the calculated values tan $\phi_b$ and cos $\Delta_b$ roughly match each other, the corresponding values of the individual film thicknesses T1, T2, T3 and T4 and the individual void rates V1, V2, V3 and V4 are deduced to be the measurement values of the film thicknesses and the void rates of the first, second, third and fourth layers. If, on the other hand, there is an error between the measurement values tan $\phi_a$ and cos $\Delta_a$ and the calculated values tan $\phi_b$ and cos $\Delta_b$, the individual values used for substitution in the model function are varied as appropriate and graph fitting is implemented repeatedly to reduce the error. Thus, the individual film thicknesses T1, T2, T3 and T4 and the void rates V1, V2, V3 and V4 obtained through the graph fitting process as indicated in FIG. 6 are used in substitution in expression (1) to calculate the total void rate X.

Figure 7:
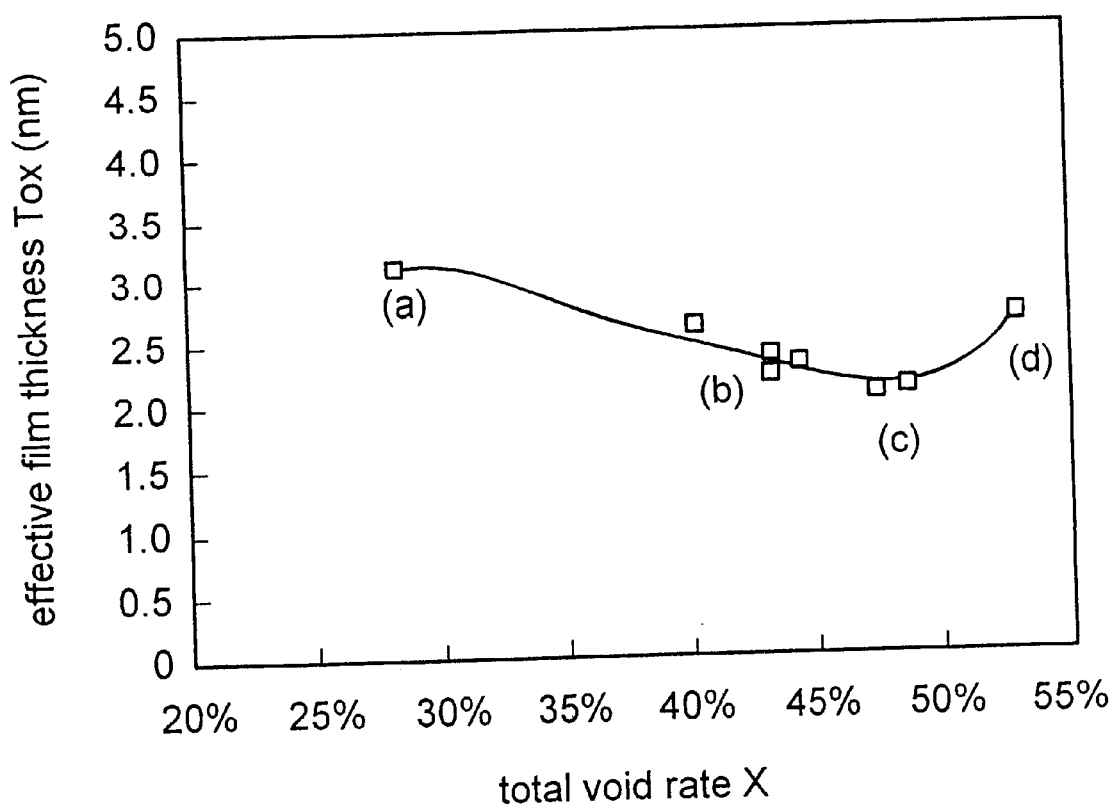
FIG. 7 presents a graph illustrating the relationship between the total void rate X obtained through the spectro-ellipsometry and the effective film thickness Tox calculated through oxide film thickness conversion for polysilicon films formed under various conditions.
Figure 8A:
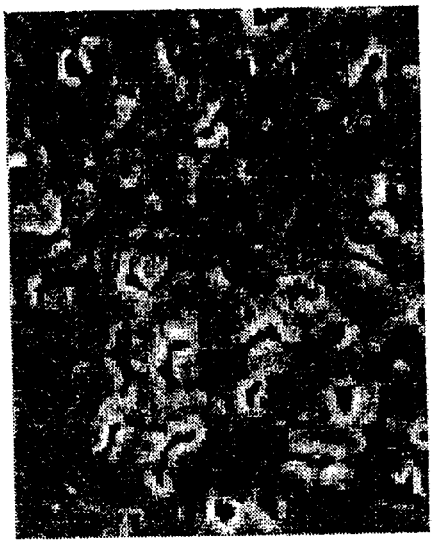
FIG. 8 presents photographs of the polysilicon films (a), (b), (c) and (d) in FIG. 7 observed through an SEM.
Figure 8B:
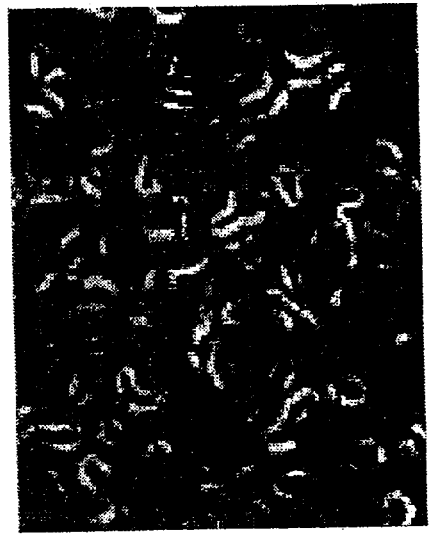
Figure 8C:
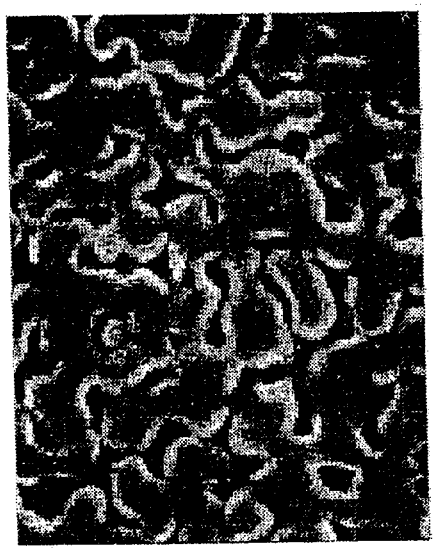
Figure 8D:

Measurement of the surface form of the polysilicon film is then enabled based upon the correlation between the total void rate X and the polysilicon film surface form. FIG. 7 presents a graph of the relationship between the total void rate X obtained through the measurement performed by the spectro-ellipsometer and the effective film thicknesses Tox calculated through oxide film thickness conversion for polysilicon films formed under various conditions. FIGS. 8(a), 8(b), 8(c) and 8(d) are SEM photographs of polysilicon films (a), (b), (c) and (d) in FIG. 7. The smallest effective film thickness Tox (i.e., the largest capacity) is achieved when the total void rate X is within the range of 45~50%, and FIG. 8(c) presents the SEM photograph of the corresponding polysilicon film. The photographs showed that as the total void rate X changes, the form of the polysilicon film also changes. As the capacitor capacity increases in a semiconductor device having capacitors such as a DRAM, the length of time over which data are held extends, to achieve an improvement in the device performance. The capacitor capacity is normally improved by using a film achieving a higher dielectric constant to constitute the capacitors (the film in which the electric charge is stored, an Si nitride film in this example) or by increasing the film surface area. As further miniaturization of semiconductor devices has been achieved in recent years, it has become increasingly difficult to allocate a large area to be occupied by capacitors. Thus, by using a polysilicon film that makes it possible to secure a large surface area to be occupied by the capacitor electrodes, the surface area of the Si nitride film deposited over the polysilicon film can be increased to achieve an increase in the capacitor capacity. The polysilicon film achieving the largest surface area with the total void rate X within the range of 45~50% can be adopted as ideal capacitor base electrode in order to increase the capacity.

Figure 13:
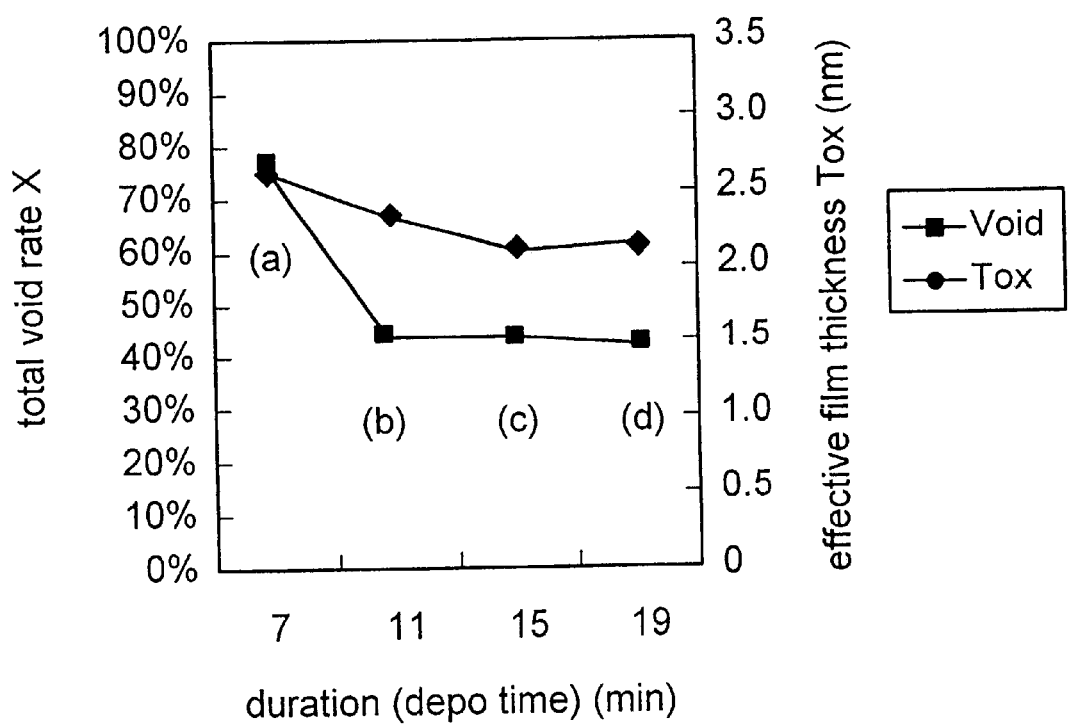
FIG. 13 presents a graph of the relationship between the total void rate X and the effective film thickness Tox achieved by varying the film formation duration during the polysilicon film formation in implementation 1.
Figure 14A:
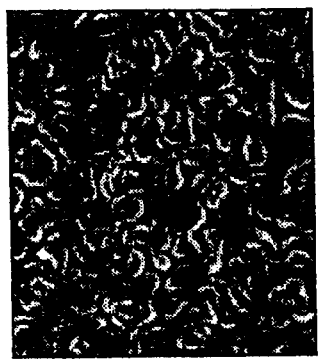
FIG. 14 presents photographs of the polysilicon films (a), (b), (c) and (d) in FIG. 13 observed through an SEM.
Figure 14B:
Figure 14C:
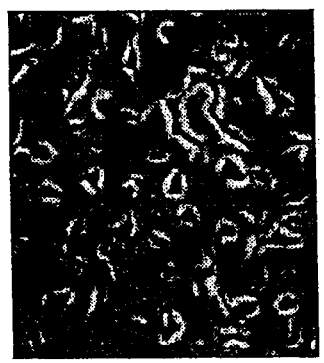
Figure 14D:

FIG. 9 shows changes in the total void rate X and the effective film thickness Tox occurring when the temperature is varied during the formation of the polysilicon film and FIGS. 10(a), (b) and (c) present SEM photographs of the polysilicon films formed at varying temperature settings. In addition, FIG. 11 shows changes in the total void rate X and the effective film thickness Tox occurring when the pressure is varied during the formation of the polysilicon film and FIGS. 12(a), (b) and (c) present SEM photographs of the polysilicon film formed at varying pressure settings. FIG. 13 shows changes in the total void rate X and the effective film thickness Tox occurring when the film formation duration is varied during the formation of the polysilicon film and FIGS. 14(a), (b), (c) and (d) present SEM photographs of the polysilicon films formed at varying film formation duration settings. By controlling the total void rate X in this manner, the polysilicon film achieving a correct surface form can be formed.

After exposing the polysilicon film constituting a semiconductor thin film to IPA vapor and then drying the polysilicon film, a quantitative analysis of IPA released from the polysilicon film was conducted through GC. Mass to indirectly measure the surface form of the polysilicon film. As in implementation 1, a thermal oxide film was developed at the surface of a semiconductor substrate over a thickness of 50 nm and a polysilicon film was formed over the thermal oxide film as a semiconductor thin film. Then, GC. Mass measurement was conducted on the polysilicon film. The measurement was performed by forming a polysilicon film on a semiconductor substrate under various conditions as in implementation 1.

Figure 15:
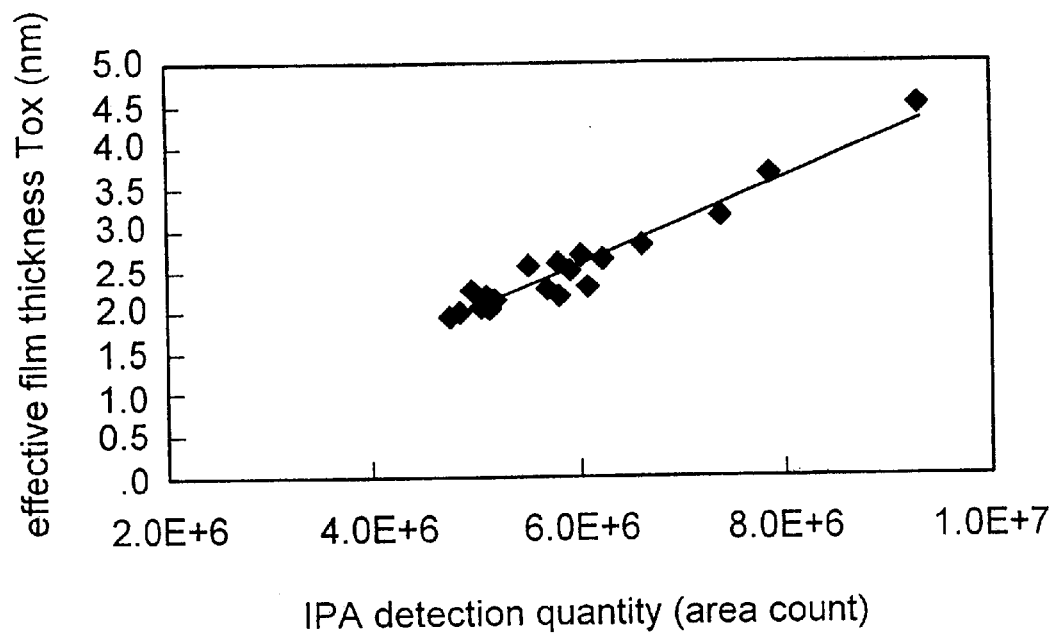
FIG. 15 presents a graph of the relationship achieved in implementation 2 between the IPA detection quantity and the effective film thickness Tox calculated through oxide film thickness conversion for polysilicon films formed under various conditions.

FIG. 15 shows the relationship between the IPA detection quantity (area count) obtained through the GC. Mass measurement and the effective film thicknesses Tox calculated through oxide film thicknesses conversion for polysilicon films formed under the various conditions. It is confirmed that as the IPA detection quantity increases, the effective film thickness Tox also increases. Thus, the surface form of the polysilicon film can be indirectly ascertained in conformance to the IPA detection quantity.

Next, the film thickness value, the reflectance and the G.O.F. (good of fit: numerical value representing reliability of measurement results) of the polysilicon film constituting the semiconductor thin film were measured on a thin film measurement device that measures film thicknesses by using UV light, e.g., the "UV-1050" manufactured by Prometrics Inc. As in implementations 1 and 2, a thermal oxide film was developed over a thickness of 50 nm on the surface of the semiconductor substrate and a polysilicon film to constitute a semiconductor thin film was formed over the thermal oxide film. The surface form of the polysilicon film was then measured based upon the reflectance of UV light. As in implementations 1 and 2, the measurement was conducted by forming polysilicon films on semiconductor substrates under various conditions.

Figure 16:
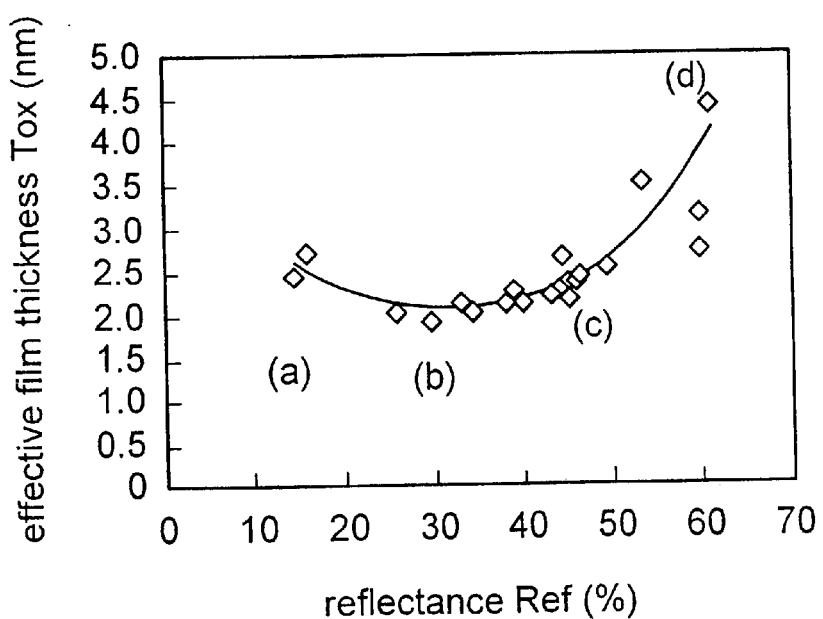
FIG. 16 presents a graph of the relationship between the reflectance Ref and the effective film thickness Tox calculated through oxide film thickness conversion achieved in implementation 3.
Figure 17A:
FIG. 17 presents photographs of the polysilicon films (a), (b), (c) and (d) in FIG. 16 observed through an SEM.
Figure 17B:
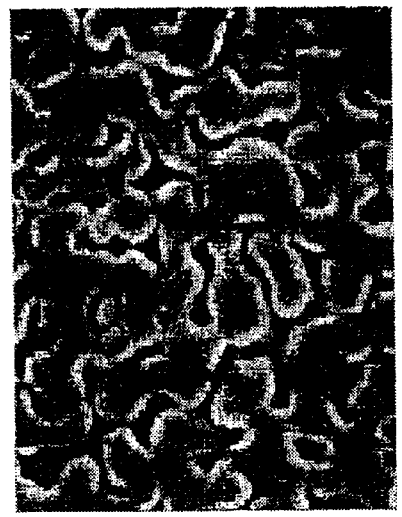
Figure 17C:
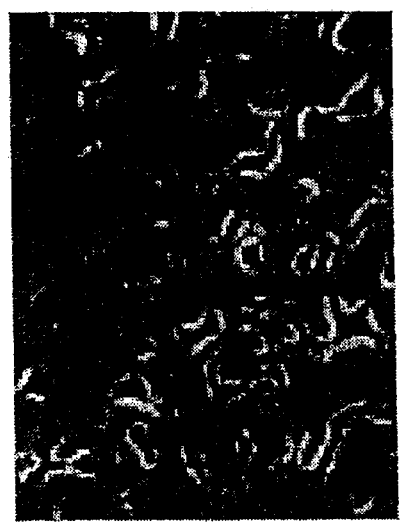
Figure 17D:

FIG. 16 presents a graph of the relationship between the reflectances Ref obtained through the measurement of the individual polysilicon films performed on the "UV-1050" and the effective film thicknesses Tox calculated through oxide film thickness conversion. FIGS. 17(a), (b), (c) and (d) respectively present SEM photographs of the polysilicon films (a), (b), (c) and (d) in FIG. 16. As FIG. 16 indicates, the smallest effective film thickness Tox (i.e., the largest capacity) is achieved when the reflectance Ref is approximately 30%, and the surface form of the corresponding polysilicon film is as shown in FIG. 17(b). As the diameter of the polysilicon particles become smaller, the reflectance Ref increases.

Figure 20:
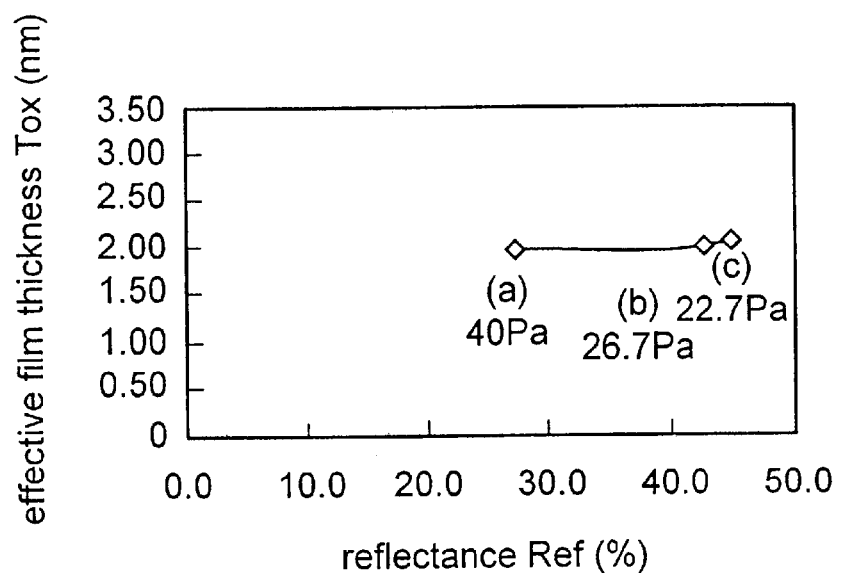
FIG. 20 presents a graph of the relationship between the reflectance Ref and the effective film thickness Tox achieved by varying the film formation pressure during the polysilicon film formation in implementation 3.
Figure 21A:
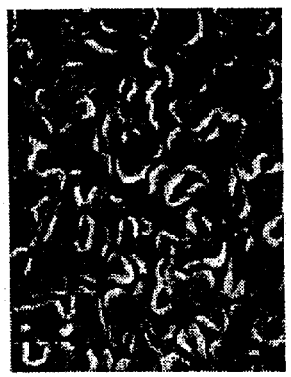
FIG. 21 presents photographs of the polysilicon films (a), (b) and (c) in FIG. 20 observed through an SEM.
Figure 21B:
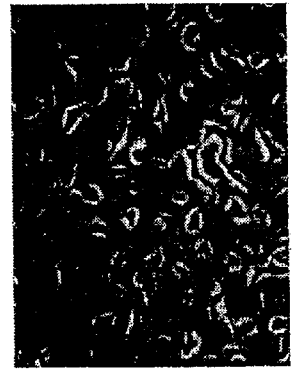
Figure 21C:
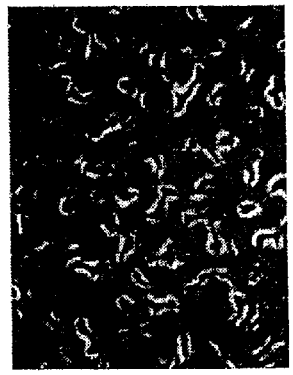

FIG. 18 shows changes in the reflectance Ref and the effective film thickness Tox occurring when the temperature is varied during the polysilicon film formation, and FIGS. 19(a), (b) and (c) respectively present SEM photographs of the polysilicon films formed at varying temperature settings. In addition, FIG. 20 shows changes in the reflectance Ref and the effective film thickness Tox occurring when the pressure is varied during the polysilicon film formation, and FIGS. 21(a), (b) and (c) respectively present SEM photographs of the polysilicon films formed at varying temperature settings. FIG. 22 shows changes in the reflectance Ref and the effective film thickness Tox occurring when the film formation duration is varied during the polysilicon film formation, and FIGS. 23(a), (b) and (c) respectively present SEM photographs of the polysilicon films formed at varying duration settings. By controlling the reflectance in this manner, a correct surface form can be achieved for the polysilicon film.

As explained above, according to the present invention, the surface form of a semiconductor thin film formed on the surface of a semiconductor substrate can be measured easily and quickly in correspondence to the total void rate of the semiconductor thin film or the IPA detection quantity of IPA released from the semiconductor thin film, to enable control of the surface form of the semiconductor thin film. Thus, consistency is achieved in the degree/height of indentations and projections formed at the surface of capacitor electrodes in an DRAM or the like to realize a consistent charge storage capacity.

The entire disclosure of Japanese Patent Application No. 2000-55603 filed on Mar. 1, 2000 including specification, claims, drawings and summary is incorporated herein by reference in its entirety.

What is claimed is:

1. A method of measuring surface form of a semiconductor thin film, wherein:

IPA (isopropyl alcohol) is uniformly deposited on a surface of said semiconductor thin film formed at a surface of a semiconductor substrate, a quantitative analysis of IPA released from said surface of said semiconductor thin film is performed, and said surface form of said semiconductor thin film is measured based upon a quantity of IPA released as detected during the quantitative analysis of IPA.

2. A method of measuring the surface form of a semiconductor thin film according to claim 1, wherein:

the IPA is deposited over said surface of said semiconductor thin film by exposing said semiconductor thin film to IPA vapor.

3. A method of measuring the surface form of a semiconductor thin film according to claim 1, wherein:

said IPA quantitative analysis is conducted through gas chromatography.

4. A method of measuring the surface form of a semiconductor thin film according to claim 1, wherein:

said semiconductor thin film is a polysilicon film.

5. A method of measuring the surface form of a semiconductor thin film according to claim 4, wherein:

said polysilicon film is formed at a surface of a silicon oxide film formed at said surface of said substrate.

6. A method of measuring surface form of a semiconductor thin film comprising:

uniformly depositing isopropyl alcohol on a surface of the semiconductor thin film;

determining an amount of released isopropyl alcohol that releases from the surface of the semiconductor thin film; and determining the surface form of the semiconductor thin film using a previously determined relationship between released isopropyl alcohol quantity and effective semiconductor thin film thickness, and the determined amount of released isopropyl alcohol.

7. The method of measuring surface form of a semiconductor thin film of claim 6, wherein the semiconductor thin film is polysilicon.

8. The method of measuring surface form of a semiconductor thin film of claim 7, wherein the polysilicon is formed on an oxide film.

9. The method of measuring surface form of a semiconductor thin film of claim 6, further comprising drying the deposited isopropyl alcohol on the surface of the semiconductor thin film before said determining an amount of released isopropyl alcohol.

10. The method of measuring surface form of a semiconductor thin film of claim 6, wherein said uniformly depositing isopropyl alcohol comprises exposing the surface of the semiconductor thin film to an isopropyl alcohol vapor.

11. The method of measuring surface form of a semiconductor thin film of claim 6, wherein said determining an amount of released isopropyl alcohol comprises gas chromatography.

* * * * *